United States Patent [19]

Bush

[11] Patent Number: 5,709,644
[45] Date of Patent: Jan. 20, 1998

[54] IMPLANTABLE SUTURE SLEEVE MODIFIED TO REDUCE TISSUE INGROWTH

[75] Inventor: M. Elizabeth Bush, Fremont, Calif.

[73] Assignee: Pacesetter, Inc., Sunnyvale, Calif.

[21] Appl. No.: 663,832

[22] Filed: Jun. 14, 1996

[51] Int. Cl.$^6$ ...................................... A61N 5/00
[52] U.S. Cl. .................. 600/3; 604/174; 607/116
[58] Field of Search ................... 600/1-8; 604/174, 604/175; 607/122, 126, 116, 120

[56] References Cited

U.S. PATENT DOCUMENTS

| | | | |
|---|---|---|---|
| 3,835,864 | 9/1974 | Rasor et al. | |
| 4,891,165 | 1/1990 | Suthanthiran | 600/1 X |
| 5,059,166 | 10/1991 | Fischell et al. | 600/3 |
| 5,152,298 | 10/1992 | Kreyenhagen et al. | 607/116 |
| 5,176,617 | 1/1993 | Fischell et al. | 600/3 |
| 5,176,907 | 1/1993 | Leong | 424/78.08 |
| 5,199,939 | 4/1993 | Dake et al. | 600/3 |
| 5,282,781 | 2/1994 | Liprie | 600/8 X |
| 5,411,550 | 5/1995 | Herweck et al. | 623/1 |
| 5,439,485 | 8/1995 | Mar et al. | 607/119 |
| 5,503,614 | 4/1996 | Liprie | 600/7 |

OTHER PUBLICATIONS

"Isostent Radioisotope Stent Expanded Scope of Use By Physicians", *MDDI Reports—The Gray Sheet*, Jul. 22, 1996, pp. I&W-9.

"Less-Invasive Techniques may Dominate Cardiovascular Therapy", *Cardiovascular Device Update*, Apr. 1996, pp. 1-16.

*Primary Examiner*—Jennifer Bahr
*Assistant Examiner*—Samuel Gilbert
*Attorney, Agent, or Firm*—Steven M. Mitchell; M. Elizabeth Bush

[57] ABSTRACT

An implantable suture sleeve for use with an implantable lead with a pacemaker/cardioverter/defibrillator lead. Since irradiation from a radioisotope source is capable of inhibiting the growth of hyperproliferating cells as compared with normal cells, a radioisotope material which is incorporated into the lead can be used to decrease the rate of fibrotic growth. The radioisotope may be located inside the suture sleeve, alloyed into or coated onto the metal from which a wire or coil within the suture sleeve is made, or molded into the rubber of the suture sleeve. Beta emitting radioisotopes having a half-life between 1 and 100 days would be best suited as the radioactive material due to their comparatively short range of action within human tissue, and because of their comparatively short half-life.

14 Claims, 4 Drawing Sheets

IMPLANTABLE SUTURE SLEEVE MODIFIED TO REDUCE TISSUE INGROWTH

FIELD OF THE INVENTION

The present invention relates generally to body implantable electrical leads, and more specifically to an implantable lead having a suture sleeve modified with a radioactive isotope to inhibit fibrotic tissue growth.

BACKGROUND OF THE INVENTION

The use of implantable electrical leads to diagnose or treat cardiac arrhythmias is well accepted. Implanted pacing and defibrillation are normally accomplished by passing a current between at least a pair of implanted electrodes. Electrical current is supplied to the electrodes by a battery powered pulse generator implanted under the skin of the patient, either in the abdominal or pectoral region. The electrode an arrangement may include a combination of intravenous, endocardial, epicardial, and/or subcutaneous leads. For example, bipolar pacing and sensing are generally accomplished using two closely spaced electrodes positioned transvenously within the atrium or ventricle or on the epicardium. Unipolar pacing is typically between an endocardial electrode (atrial or ventricular) and the pacemaker pulse generator housing. For implantable cardioverter defibrillators (ICD), a typical lead system includes one large surface area right ventricular (RV) endocardial defibrillation electrode, and a second electrode positioned subcutaneously (SQ), such as a pulse generator housing electrode or patch electrode. A defibrillation electrode may be positioned transvenously within the superior vena cava (SVC), either in place of or in addition to the SQ electrode. Various other electrode combinations are common for both pacing and defibrillation.

A plurality of pliant fixation tines which extend at an acute angle to the lead body from the distal tip of the lead may be used to fix transvenous endocardial leads within the heart. When the lead is extended into the right ventricle, the tines act as an anchor catching in the trabeculae of the heart wall. Over time, the growth of tissue around the tines will further act to secure the lead tip in place. Epicardial and SQ electrodes are typically sutured in place. For additional stabilization, each lead generally has one or more suture sleeves for anchoring the lead body to the venous entry site (for a transvenous lead), entrance to the pericardial space (for an epicardial lead), or to other tissues. The suture sleeve protects the lead body insulation and conductor from cutting and crushing by the ligature used to tie down the lead.

A recurrent problem with chronically implanted leads is excessive fibrotic tissue growth along the lead body. In some instances, lead removal may be necessitated by infection, fatigue failures, insulation abrasion, or other problems. Excessive adhesions along the lead body results in a lead that is very difficult to extract. Various techniques for extracting adherent leads have been devised, including slow traction (hanging progressively heavier weights on the lead and waiting) and locking guidewire techniques through the venous implant site or a femoral route using specially-designed hardware. In some cases the adhesions are so extensive that the lead may need to be removed by open heart surgery.

It is therefore an object of the invention to provide a suture sleeve for use with an implantable electrical lead which inhibits fibrotic tissue ingrowth into the lead.

SUMMARY OF THE INVENTION

The present invention uses a radioisotope in a suture sleeve of an implantable lead which can irradiate the tissue in close proximity to the implantation site of the suture sleeve to reduce the rapid tissue growth caused by trauma to the vein and other tissues from an indwelling lead. The invention is based on the knowledge that radiation therapy can reduce the proliferation of rapidly growing cancer cells in a malignant tumor. By incorporating a radioactive material having a relatively short half-life into the suture sleeve, fibrotic growth can be inhibited in the region surrounding the suture sleeve, while still allowing a certain amount of fibrosis for tip stabilization or other desired attachment points.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
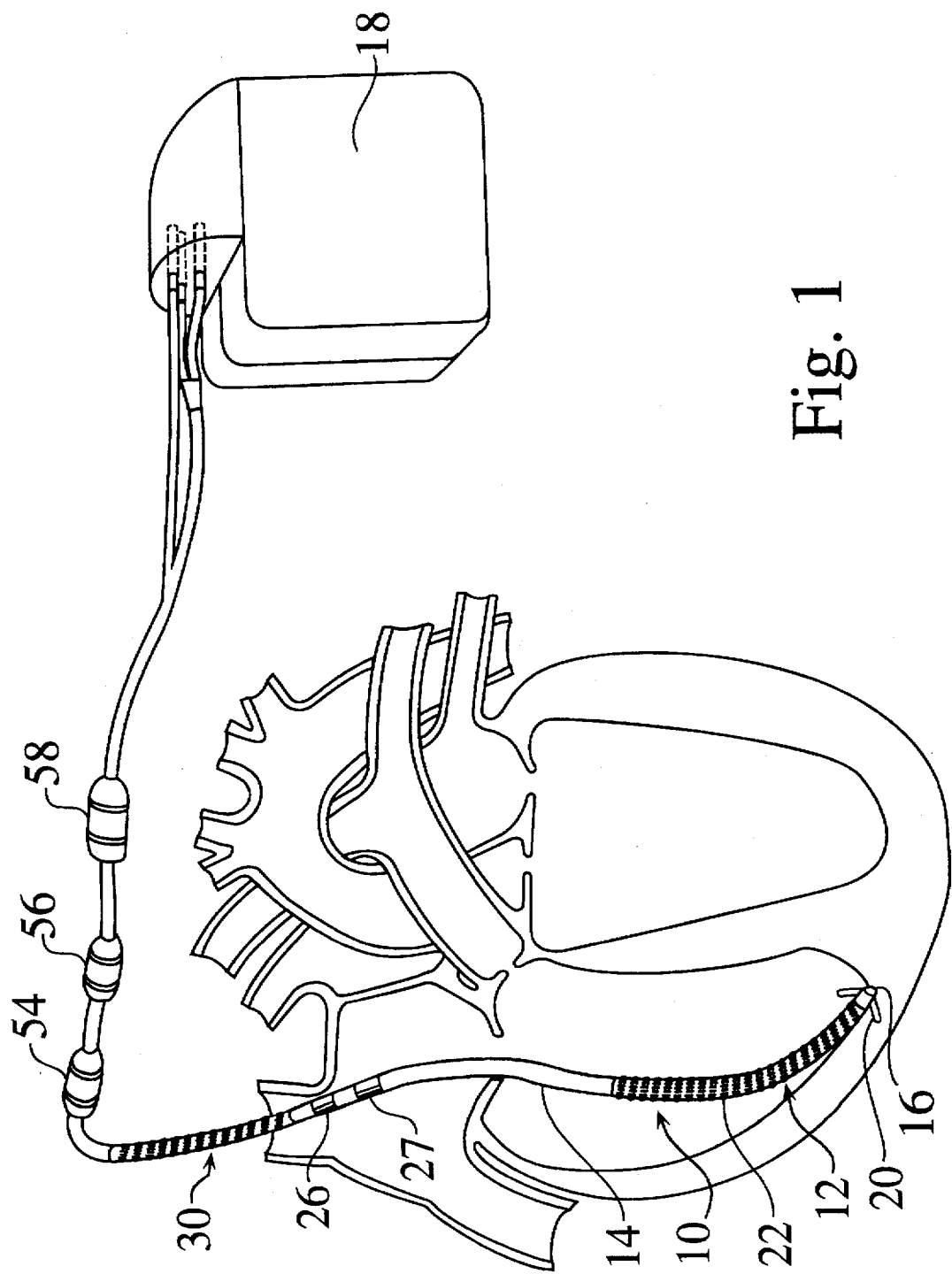
FIG. 1 shows a lead implanted in a human heart shown in partial section and having a suture sleeve of the invention.

A suture sleeve according to the invention will now be described with reference to FIGS. 1–6. An endocardial lead 10 shown in FIG. 1 includes a defibrillation/sensing electrode 12 proximal of the distal end of lead 10 and extending along the lead body 14, and a pacing/sensing electrode 16 at the distal tip of lead 10. The proximal end of lead is connected to an ICD 18 of known construction. Lead 10 may include tines 20 to aid in fixation of the distal end within the apex of the patient's heart. Alternatively, a helical screw may be provided as a fixation device. Lead 10 also includes three suture sleeves 54, 56, 58 which may be positioned along the length of lead body 14 at the time of implant for anchoring lead body 14 to the venous entry site and to other tissue. Sutures sleeves 54, 46, 58 may be molded or extruded from silicone rubber, polyurethane, a fluoropolymer, or the like.

Defibrillation/sensing electrode 12 is in the form of a conductive electrode coil 22 wound around the periphery of lead body 14. Electrode coil 22 may be of the type disclosed in U.S. Pat. No. 5,439,485 to Mar et al. entitled Flexible Defibrillation Electrode of Improved Construction, which is assigned to the assignee of the present application and is incorporated herein by reference. Other known electrode configurations may also be used. Electrode coil 22 is connected to a conductor within the lead, which is in turn connected to a connector for making electrical and mechanical connection to ICD 18. Also included on lead 10 are two atrial electrodes 26, 27 which may be used for sensing and/or pacing and are located approximately 14 centimeters from the distal end of lead 10.

Defibrillation electrode 12 of lead 10 may be used in conjunction with a SQ electrode such as the housing of ICD 18 or a flexible patch. In addition to or instead of the SQ electrode, an SVC electrode 30 may be used, and may be located on lead 10 or may be on a separate lead.

Figure 2:
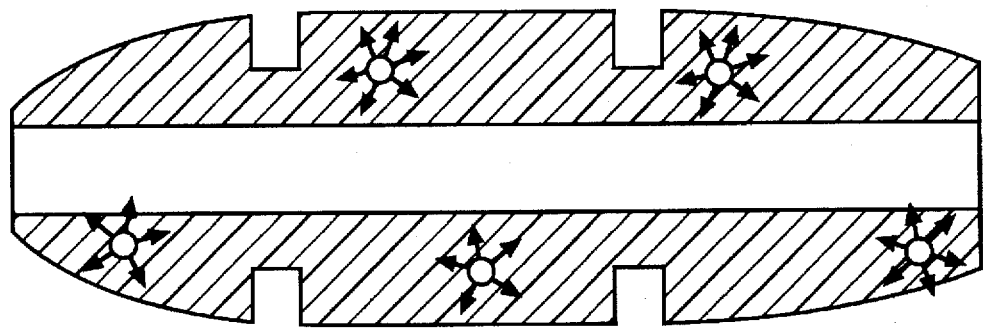
FIG. 2 is a cross section through a suture suture sleeve which has had a radioisotope mixed into the uncured rubber prior to molding.

FIG. 2 is a cross section through suture suture sleeve 54 which has had a radioisotope mixed into the uncured rubber prior to molding. The arrows pointing outward from the cross section indicate the omnidirectional emission of particles from the molded rubber. The purpose of this radiation is to decrease the rate of proliferative cell growth of the traumatized venous wall or other tissue surrounding suture sleeve 54. Thus it would be expected that the lead will remain explantable if necessary without having to resort to extraordinary means. Because a suture sleeve is generally implanted at the venous entry site, fibrotic growth would be inhibited in that region by using a sleeve having radioactive material in it.

The radioisotope used for this purpose may be an alpha, beta or gamma emitter. The half-life would ideally be between 10 hours and 100 days. An optimum emitter might be a beta emitting isotope such a vanadium which has a half-life of 16 days and only 8% of its emitted energy is from gamma radiation. The ideal attribute of a beta emitter is that the radiation does not travel very far in human tissue. Thus only the tissue in close proximity to the radioisotope lead will be affected. Furthermore only moderate levels of radiation are desired since it is known that very high levels can cause injury to nonproliferating tissues.

One drawback of using a radioisotope with a short half-life is that manufacturing and storage of the lead would pose some logistical problems. From the time the lead is manufactured, either using a radioisotope directly or irradiating material to form a radioisotope, to the time the lead is implanted in the patient, a certain amount of radioisotope will have decayed. Any delay in shipping, or time spent on the shelf of a hospital supply room or company stock room would decrease the amount of radioisotope available in the lead for therapeutic use. These logistical problems would be lessened by using a radioisotope with a half-life longer than 100 days.

Figure 3:
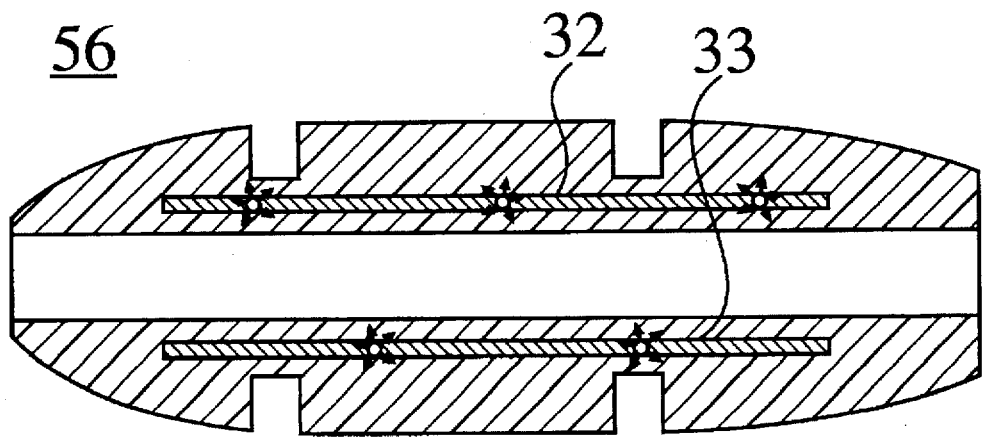
FIG. 3 is a suture sleeve sleeve showing embedded wires made of a radioisotope material.

FIG. 3 is a cross section through suture sleeve 56 showing small embedded wires 32, 33 made of a radioisotope material. Wires 32, 33 may be from a pure metal or alloy which has been irradiated so that it has become radioactive; i.e., it is a radioisotope, and are completely encapsulated by silicone rubber. Alternatively, wires 32, 33 may be encapsulated by polyurethane, fluoropolymer, or other biocompatible material. The arrows pointing outward from the cross section indicate the omnidirectional emission of particles from wires. The purpose of this radiation is to decrease the rate of proliferative cell growth of the traumatized venous wall or other surrounding tissues. Thus it would be expected that the lead will remain explantable if necessary without having to resort to extraordinary means.

Wires may alternatively be made from a metal into which is alloyed an element that can be made into a radioisotope. For example, phosphorus, a 14.3 day half-life beta emitter, could be alloyed into steel which could be used for wires.

Figure 4:
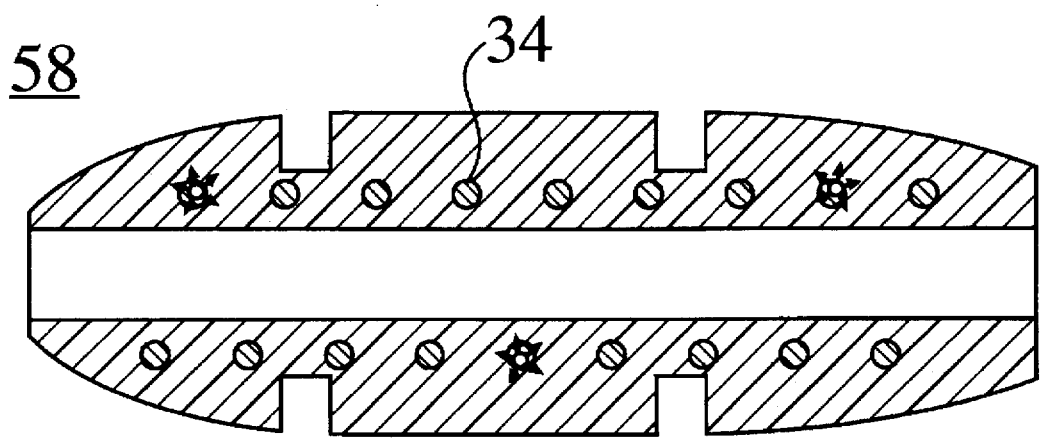
FIG. 4 is a cross section of suture sleeve having a coil of radioactive wire encapsulated within.

FIG. 4 is a cross section of suture sleeve 58 which has a coil 34 of radioactive wire encapsulated therein.

Figure 5:
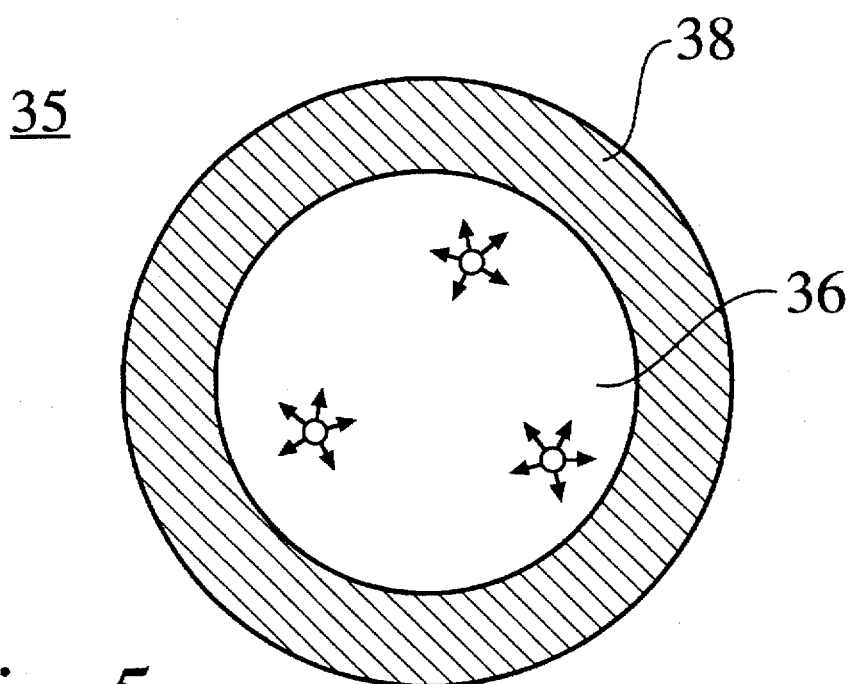
FIG. 5 is cross section of a wire of either the wire of FIG. 3 or the coil of FIG. 4.

FIG. 5 is a cross section showing the structure 35 of either wires 32, 33 of suture sleeve 56 of FIG. 3 or of coil 34 of suture sleeve 58 of FIG. 4. Structure 35 is made from a radioisotope core 36, such as Au 198 (half-life 2.7 days), within an outer covering 38, such as PtIr, that has the attributes that are desirable for molding into suture sleeve 56 or 58. This structure may be made by the drawn filled tube (DFT) process of Fort Wayne Metals (Fort Wayne, In.) or by plating or depositing outer covering 38 onto radioisotope core 36.

Figure 6:
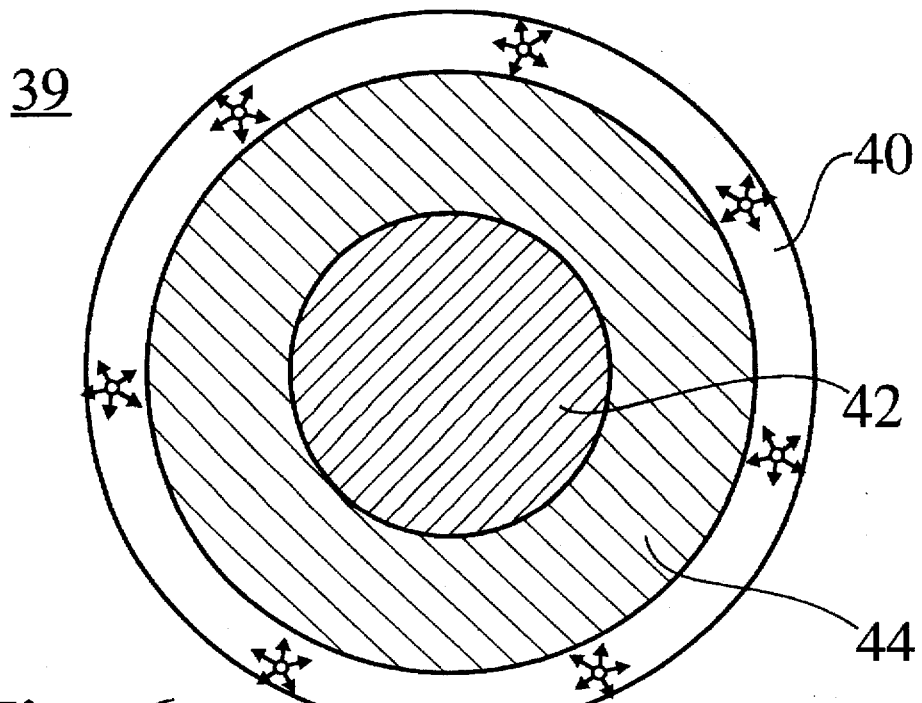
FIG. 6 is a cross section of an alternative wire of either the wire of FIG. 3 or the coil of FIG. 4.

FIG. 6 is a cross section of an alternative structure 39 of either wires 32, 33 of suture sleeve 56 of FIG. 3 or of coil 34 of suture sleeve 58 of FIG. 4. A radioisotope jacket 40, such as the beta emitting isotope gold 198, forms the outer layer of wires 32, 33 or coil 34. The structure shown is DFT having a silver core 42 with a tube of MP35N 44 drawn over it. Radioisotope jacket 40 may also be formed as a drawn tube, or may be plated onto the Ag/MP35N DFT structure.

It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. An implantable suture sleeve comprising:
   an elastomeric body for protecting a lead body from a ligature, said elastomeric body forming a lumen for receiving said lead body and having means for receiving said ligature; and
   a radioactive material within said body that emits radiation that can reduce the proliferation of cells.

2. The implantable suture sleeve of claim 1 in which the radioactive material emitting the radiation is a radioisotope.

3. The implantable suture sleeve of claim 2 wherein said radioisotope is a beta particle emitting radioisotope.

4. The implantable suture sleeve of claim 2 wherein said radioisotope has a half-life of less than 100 days.

5. The implantable suture sleeve of claim 1 made by the process of:
   (a) mixing said radioactive material into uncured rubber; and
   (b) molding said uncured rubber to form said elastomeric body.

6. The implantable suture sleeve of claim 1 wherein said radioactive material comprises plating of a wire located within said elastomeric body.

7. The implantable suture sleeve of claim 6 wherein said wire is coiled.

8. The implantable suture sleeve of claim 1 wherein said radioactive material comprises a core of a wire located within said elastomeric body.

9. The implantable suture sleeve of claim 8 wherein said wire is coiled.

10. The implantable suture sleeve of claim 1 and further including one or more wires comprising said radioactive material.

11. The implantable suture sleeve of claim 1 wherein said elastomeric body comprises insulating tubing, and wherein said radioactive material is extruded into said insulating tubing.

12. The implantable suture sleeve of clam 1 wherein said radioactive material is covered by a biocompatible material.

13. The implantable suture sleeve of claim 12 wherein said biocompatible material is chosen from the group consisting of silicone rubber, fluoropolymer, and polyurethane.

14. The implantable suture sleeve of claim 12 wherein said biocompatible material is a metal.

\* \* \* \* \*